US012618844B2

(12) United States Patent (10) Patent No.: US 12,618,844 B2
Hanna et al. (45) Date of Patent: May 5, 2026

(54) CANCER

(71) Applicant: Imperial College Innovations Limited, London (GB)

(72) Inventors: George Hanna, London (GB); Sophie Doran, London (GB)

(73) Assignee: Imperial College Innovations Limited, London (GB)

( * ) Notice: Subject to any disclaimer, the term of this patent is extended or adjusted under 35 U.S.C. 154(b) by 895 days.

(21) Appl. No.: 17/793,374

(22) PCT Filed: Jan. 18, 2021

(86) PCT No.: PCT/GB2021/050104
§ 371 (c)(1),
(2) Date: Jul. 15, 2022

(87) PCT Pub. No.: WO2021/144589
PCT Pub. Date: Jul. 22, 2021

(65) Prior Publication Data
US 2023/0068371 A1 Mar. 2, 2023

(30) Foreign Application Priority Data
Jan. 17, 2020 (GB) .................................... 2000739

(51) Int. Cl.
*G01N 33/575* (2026.01)
*G01N 33/497* (2006.01)
*G01N 33/5753* (2026.01)
(52) U.S. Cl.
CPC ..... *G01N 33/57585* (2026.01); *G01N 33/497* (2013.01); *G01N 33/5753* (2026.01); *G01N 33/4975* (2024.05)

(58) Field of Classification Search
CPC ........... G01N 2560/00; G01N 2800/52; G01N 33/497; G01N 33/4975; G01N 33/57407; G01N 33/57446; G01N 33/57488
See application file for complete search history.

(56) References Cited

U.S. PATENT DOCUMENTS 6,027,550 A * 2/2000 Vickery ................. B01D 53/10
95/110
2013/0150261 A1* 6/2013 Haick ................... G01N 33/497
585/16

(Continued)

FOREIGN PATENT DOCUMENTS

GB 2584300 A 12/2020
WO WO2019053414 3/2019

(Continued)

OTHER PUBLICATIONS

Adam, Mina E., et al. "Mass-spectrometry analysis of mixed-breath, isolated-bronchial-breath, and gastric-endoluminal-air volatile fatty acids in esophagogastric cancer." Analytical chemistry 91.5 (2019): 3740-3746.

(Continued)

*Primary Examiner* — Jennifer Wecker
(74) *Attorney, Agent, or Firm* — Dickinson Wright PLLC

(57) ABSTRACT
The invention relates to biomarkers, and to novel biological markers for diagnosing cancer. In particular, the invention relates to the use of these compounds as diagnostic and prognostic markers in assays for detecting cancer, such as oesophagogastric cancer, and corresponding methods of detection. The invention also relates to methods of determining the efficacy of treating these diseases with a therapeutic agent. The assays are qualitative and/or quantitative, and are adaptable to large-scale screening and clinical trials.

10 Claims, 1 Drawing Sheet

(56) References Cited

U.S. PATENT DOCUMENTS

2018/0156775 A1*  6/2018  Chou ................... A61B 5/0836
2018/0209978 A1*  7/2018  Postrel ................ A61K 35/765
2019/0317073 A1   10/2019 Horvath
2020/0029858 A1*  1/2020  Reddy ................... G16H 40/67
2021/0341461 A1* 11/2021  Allsworth ............. A61B 5/082

FOREIGN PATENT DOCUMENTS

WO        WO2019102221       5/2019
WO        WO-2020049300 A1 *  3/2020   ......... A61K 51/1231

OTHER PUBLICATIONS

International Search Report and Written Opinion for Application No. PCT/GB2021/050104 mailed on May 7, 2022, 17 pages.
Kumar, Sacheen, et al. "Mass spectrometric analysis of exhaled breath for the identification of volatile organic compound biomark-ers in esophageal and gastric adenocarcinoma." Annals of surgery 262.6 (2015): 981-990.
Kumar, Sacheen, et al. "Selected ion flow tube mass spectrometry analysis of exhaled breath for volatile organic compound profiling of esophago-gastric cancer." Analytical chemistry 85.12 (2013): 6121-6128.
Markar, Sheraz R., et al. "Assessment of a noninvasive exhaled breath test for the diagnosis of oesophagogastric cancer." *JAMA oncology* 4.7 (2018): 970-976.
Nishiumi, Shin, et al. "Metabolomics for biomarker discovery in gastroenterological cancer." Metabolites 4.3 (2014): 547-571.
Silva, C. L., M. Passos, and J. S. Câmara. "Investigation of urinary volatile organic metabolites as potential cancer biomarkers by solid-phase microextraction in combination with gas chromatography-mass spectrometry." British journal of cancer 105.12 (2011): 1894-1904.
Suzuki, Makoto, et al. "Metabolome analysis for discovering biomark-ers of gastroenterological cancer." Journal of Chromatography B 966 (2014): 59-69.

* cited by examiner

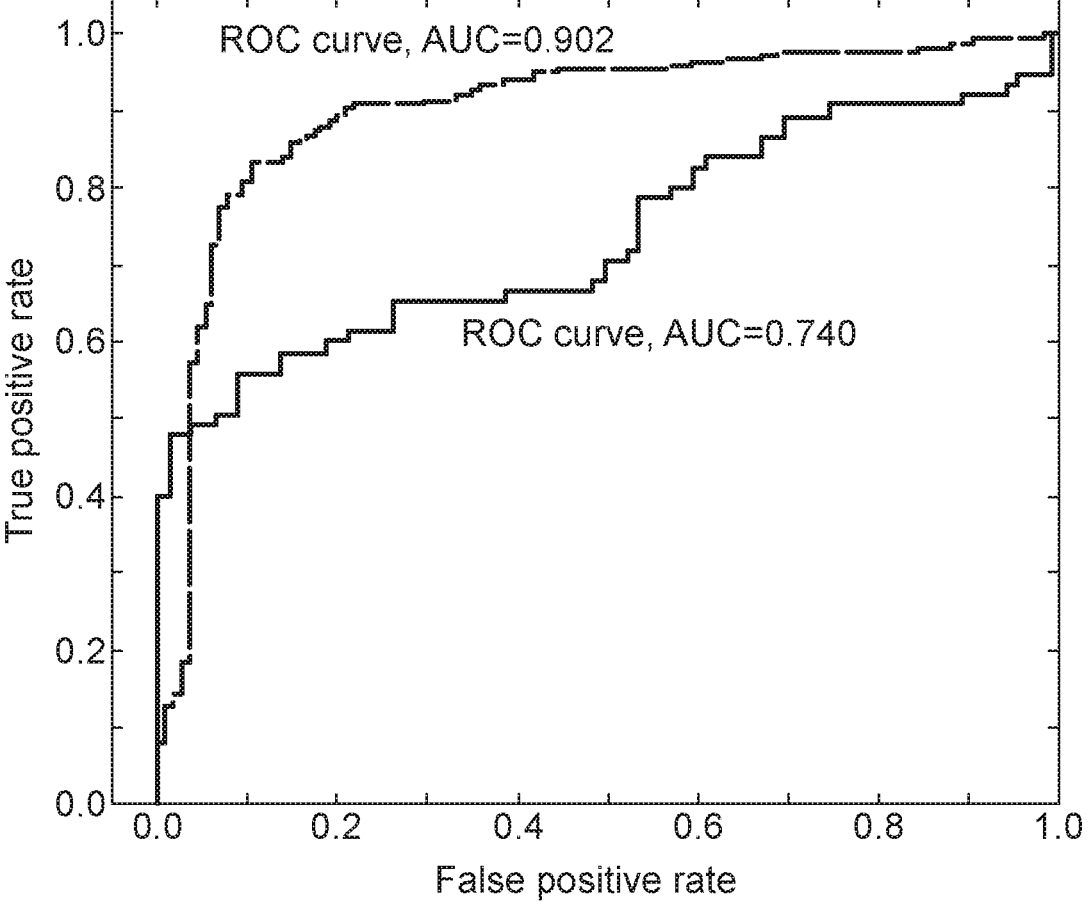

CANCER

RELATED APPLICATIONS

The present application is a U.S. national phase application under 35 U.S.C. § 371 of International Application No. PCT/GB2021/050104, filed on Jan. 18, 2021, and published as WO 2021/144589 A1 on Jul. 22, 2021; which claims the priority of GB Application No. 2000739.9, filed on Jan. 17, 2020. The content of each of these related applications is incorporated herein by reference in its entirety.

The present invention relates to cancer, and particularly although not exclusively, to detecting volatile organic compounds (VOCs) for diagnosis of, and prognostication in, oesophagogastric cancer.

The chemical analysis of volatile organic compounds (VOCs) in humans is a rapidly evolving field that has the potential to contribute to the non-invasive detection of multiple disease states. A recent systematic review on the diagnostic accuracy of VOC-based exhaled breath tests showed their potential for non-invasive cancer detection. Previous studies have reported higher concentrations of specific VOCs, within the exhaled breath, gastric content and urine of patients with oesophagogastric cancer. However, whilst several studies have suggested a role for these VOCs in important regulatory processes in oesophagogastric cancer, many of the biochemical pathways relating to their origin in humans are as yet unknown. Nevertheless, it has been postulated that the deregulated production of specific VOCs occurs directly from cancer tissues, and these VOCs may pass in to the systemic circulation with subsequent partition across the alveolar-capillary barrier. Alternatively, VOCs may be released directly by the mucosa within the aerodigestive tract. National studies have shown that about 9% of gastric and oesophageal cancers were missed during endoscopy prior to diagnosis. Accordingly, there is a need for improved techniques for diagnosing oesophagogastric cancer.

The present invention arises from the inventor's work in trying to overcome the problems associated with the prior art.

In a first aspect of the invention, there is provided a method for diagnosing a subject suffering from cancer, or a pre-disposition thereto, or for providing a prognosis of the subject's condition, the method comprising analysing the level of at least one signature compound in a bodily sample from a test subject and comparing this level with a reference level, wherein the reference level is the level of the at least one signature compound in an individual, or the average level for a group of individuals, wherein the individual or group of individuals do not suffer from cancer, wherein (i) an increase in the level of at least one signature compound selected from the group consisting of methyl 2,3,5,6-tetra-O-methyl-α-D-galactofuranoside; 1-tetradecanol; N-butyl-benzenesulfonamide; hexadecanoic acid; tetradec-5-yl ester 3,5,5-trimethyl-hexanoic acid; tetradecyl ester undec-10-ynoic acid; 1-dotriacontanol; 1-chloro-tetradecane; 4-methyloctan-1-ol; carbon monoxide; nickel; 2-ethyl-cyclohexylamine; 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediyl))diethanol; 3-methyl-thiophene; butanal; tert-butyl alcohol; and 2-methoxysuccinonitrile, or an analogue or derivative thereof, in the bodily sample from the test subject, compared to the reference, and/or (ii) a decrease in the level of at least one signature compound selected from the group consisting of 4-hydroximino-2,2,6,6-tetramethyl-1-piperidinyl ester 4-amino-benzoic acid; 4,4-dimethyl-octane; benzyl 3-deuterio-α-diazopropionate; and 1-methyl-ethyl ester formic acid, or an analogue or derivative thereof, in the bodily sample from the test subject, compared to the reference, suggests that the subject is suffering from cancer, or has a pre-disposition thereto, or provides a negative prognosis of the subject's condition.

In a second aspect, there is provided a method for determining the efficacy of a treatment a subject suffering from cancer, the method comprising analysing the level of at least one signature compound in a bodily sample from a test subject and comparing this level with a reference level, wherein the reference level is the level of the at least one signature compound in a sample taken from the subject previously, wherein (i) a decrease in the level of at least one signature compound selected from the group consisting of methyl 2,3,5,6-tetra-O-methyl-α-D-galactofuranoside; 1-tetradecanol; N-butyl-benzenesulfonamide; hexadecanoic acid; tetradec-5-yl ester 3,5,5-trimethyl-hexanoic acid; tetradecyl ester undec-10-ynoic acid; 1-dotriacontanol; 1-chloro-tetradecane; 4-methyloctan-1-ol; carbon monoxide; nickel; 2-ethyl-cyclohexylamine; 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediyl))diethanol; 3-methyl-thiophene; butanal; tert-butyl alcohol; and 2-methoxysuccinonitrile, or an analogue or derivative thereof, in the bodily sample from the test subject, compared to the reference, or (ii) an increase in the level of at least one signature compound selected from the group consisting of 4-hydroximino-2,2,6,6-tetramethyl-1-piperidinyl ester 4-amino-benzoic acid; 4,4-dimethyl-octane; benzyl 3-deuterio-α-diazopropionate; and 1-methylethyl ester formic acid, or an analogue or derivative thereof, in the bodily sample from the test subject, compared to the reference, suggests that the treatment is effective, or wherein (i) an increase in the level of at least one signature compound selected from the group consisting of methyl 2,3,5,6-tetra-O-methyl-α-D-galactofuranoside; 1-tetradecanol; N-butyl-benzenesulfonamide; hexadecanoic acid; tetradec-5-yl ester 3,5,5-trimethyl-hexanoic acid; tetradecyl ester undec-10-ynoic acid; 1-dotriacontanol; 1-chloro-tetradecane; 4-methyloctan-1-ol; carbon monoxide; nickel; 2-ethyl-cyclohexylamine; 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediyl))diethanol; 3-methyl-thiophene; butanal; tert-butyl alcohol; and 2-methoxysuccinonitrile, or an analogue or derivative thereof, in the bodily sample from the test subject, compared to the reference, or (ii) a decrease in the level of at least one signature compound selected from the group consisting of 4-hydroximino-2,2,6,6-tetramethyl-1-piperidinyl ester 4-amino-benzoic acid; 4,4-dimethyl-octane; benzyl 3-deuterio-α-diazopropionate; and 1-methylethyl ester formic acid, or an analogue or derivative thereof, in the bodily sample from the test subject, compared to the reference, suggests that the is ineffective.

The method of the first aspect may comprise treating the subject, wherein the treatment prevents, reduces or delays the progression of cancer and/or treats cancer.

According to a third aspect of the invention, there is provided a method of treating an individual suffering from cancer, said method comprising the steps of:

a) determining the level of at least one signature compound in a bodily sample from a test subject and comparing this level with a reference level, wherein the reference level is the at least one signature compound in an individual, or the average level for a group of individuals, wherein the individual or group of individuals do not suffer from cancer, wherein (i) an increase in at least one signature compound selected from the group consisting of methyl 2,3,5,6-tetra-O-methyl-α-D-galactofuranoside; 1-tetradecanol; N-butyl-benzenesulfonamide; hexadecanoic acid; tetradec-5-yl ester 3,5,5-trimethyl-hexanoic acid; tetradecyl ester undec-10-ynoic acid; 1-dotriacontanol; 1-chloro-tetradecane; 4-methyloctan-1-ol; carbon monoxide; nickel; 2-ethyl-cyclohexylamine; 3-ethyl-1-octene; ethyl lactate; tetramethyl succinimide; 6-methyl heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediye)diethanol; 3-methyl-thiophene; butanal; tert-butyl alcohol; and 2-methoxysuccinonitrile, compared to the reference, or an analogue or derivative thereof, in the bodily sample from the test subject, or (ii) a decrease in the level of at least one signature compound selected from the group consisting of 4-hydroximino-2,2,6,6-tetramethyl-1-piperidinyl ester 4-amino-benzoic acid; 4,4-dimethyl-octane; benzyl 3-deuterio-α-diazopropionate; and 1-methylethyl ester formic acid, or an analogue or derivative thereof, in the bodily sample from the test subject, compared to the reference, suggests that the subject is suffering from cancer, or has a pre-disposition thereto, or has a negative prognosis; and b) treating the test subject, wherein the treatment reduces or delays progression of cancer and/or treats cancer.

In a fourth aspect, there is provided use of at least one signature compound selected from the group consisting of methyl 2,3,5,6-tetra-O-methyl-α-D-galactofuranoside; 1-tetradecanol; N-butyl-benzenesulfonamide; hexadecanoic acid; tetradec-5-yl ester 3,5,5-trimethyl-hexanoic acid; tetradecyl ester undec-m-ynoic acid; 1-dotriacontanol; 1-chloro-tetradecane; 4-methyloctan-1-ol; carbon monoxide; nickel; 2-ethyl-cyclohexylamine; 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediye)diethanol; 3-methyl-thiophene; butanal; tert-butyl alcohol; 2-methoxysuccinonitrile; 4-hydroximino-2,2,6,6-tetramethyl-1-piperidinyl ester 4-amino-benzoic acid; 4,4-dimethyl-octane; benzyl 3-deuterio-α-diazopropionate; and 1-methylethyl ester formic acid, or an analogue or derivative thereof, as a biomarker for diagnosing a subject suffering from cancer, or a pre-disposition thereto, or for providing a prognosis of the subject's condition.

Preferably the cancer is an oesophagogastric cancer.

As described in Example 2, the inventors have shown that an increase in the level of methyl 2,3,5,6-tetra-O-methyl-α-D-galactofuranoside; 1-tetradecanol; N-butyl-benzenesulfonamide; hexadecanoic acid; tetradec-5-yl ester 3,5,5-trimethyl-hexanoic acid; tetradecyl ester undec-10-ynoic acid; 1-dotriacontanol; 1-chloro-tetradecane; 4-methyloctan-1-ol; carbon monoxide; nickel; 2-ethyl-cyclohexylamine; 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediyl)) diethanol; 3-methyl-thiophene; butanal; tert-butyl alcohol; and 2-methoxysuccinonitrile, or a decrease in the level of 4-hydroximino-2,2,6,6-tetramethyl-1-piperidinyl ester 4-amino-benzoic acid; 4,4-dimethyl-octane; benzyl 3-deuterio-α-diazopropionate; and 1-methylethyl ester formic acid, is indicative of oesophagogastric cancer. The methods, apparatus and uses described herein may also comprise analysing the level of an analogue or a derivative of the signature compounds described herein. Examples of suitable analogues or derivatives of chemical groups which may be assayed include alcohols, ketones, aromatics, organic acids and gases (such as $CO$, $CO_2$, $NO$, $NO_2$, $H_2S$, $SO_2$, $CH_4$).

When the at least one signature compound comprises nickel then the at least one signature compound may also comprise carbon monoxide. Similarly, when the at least one signature compound comprises carbon monoxide then the at least one signature compound may also comprise nickel. Accordingly, it may be understood that carbon monoxide and nickel are considered to be signature compounds when sensed together.

The at least one signature compound may be selected from the group consisting of methyl 2,3,5,6-tetra-O-methyl-α-D-galactofuranoside; 4-hydroximino-2,2,6,6-tetramethyl-1-piperidinyl ester 4-amino-benzoic acid; 1-tetradecanol; N-butyl-benzenesulfonamide; hexadecanoic acid; tetradec-5-yl ester 3,5,5-trimethyl-hexanoic acid; 4,4-dimethyl-octane; tetradecyl ester undec-10-ynoic acid; 1-dotriacontanol; benzyl 3-deuterio-α-diazopropionate; 1-methylethyl ester formic acid; 1-chloro-tetradecane; 4-methyloctan-1-ol; carbon monoxide; nickel; and 2-ethyl-cyclohexylamine, or an analogue or derivative thereof. Preferably, the at least one signature compound is selected from the group consisting of methyl 2,3,5,6-tetra methyl-α-D-galactofuranoside; 4-hydroximino-2,2,6,6-tetramethyl-1-piperidinyl ester 4-amino-benzoic acid; 1-tetradecanol; N-butyl-benzenesulfonamide; hexadecanoic acid; tetradec-5-yl ester 3,5,5-trimethyl-hexanoic acid; 4,4-dimethyl-octane; tetradecyl ester undec-10-ynoic acid; 1-dotriacontanol; and benzyl 3-deuterio-α-diazopropionate, or an analogue or derivative thereof. Most preferably, the at least one signature compound is selected from the group consisting of methyl 2,3,5,6-tetra-O-methyl-α-D-galactofuranoside; 4-hydroximino-2,2,6,6-tetramethyl-1-piperidinyl ester 4-amino-benzoic acid; 1-tetradecanol;

N-butyl-benzenesulfonamide; and hexadecanoic acid, or an analogue or derivative thereof.

The at least one signature compound may be selected from the group consisting of 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trim-ethyl-2-oxabicyclo[2.2.2]oct-5-ene; 2,2'-(ethene-1,2-diylbis (sulfanediyl))diethanol; 3-methyl-thiophene; butanal; tert-butyl alcohol; and 2-methoxysuccinonitrile, or an analogue or derivative thereof. Preferably, the at least one signature compound is selected from the group consisting of 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methyl-ene-5-hexenal; 3-methyl-1-butyne; (R)-5-methyl-2-(i-methylethylidene)-cyclohexanone; α-propyl-benzeneetha-nol; 4-methyl-1-pentene; and 1,3,3-trimethyl-2-oxabicyclo [2.2.2]oct-5-ene, or an analogue or derivative thereof. More preferably, the at least one signature compound is selected from the group consisting of 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; and nickel tetracar-bonyl, or an analogue or derivative thereof. Most preferably, the at least one signature compound is selected from the group consisting of 3-ethyl-1-octene; and ethyl lactate, or an analogue or derivative thereof.

It will be appreciated that, in their most preferred embodi-ments, the aspects involve detecting an increase and/or decrease of the same signature compounds as defined in the previous paragraphs.

An important feature of any useful biomarker used in disease diagnosis and prognosis is that it exhibits high sensitivity and specificity for a given disease. As explained in the examples, the inventors have surprisingly demon-strated that a number of signature compounds found in the exhaled breath from test subjects serve as robust biomarkers for cancer, and can therefore be used for the detection of cancer, and cancer prognosis. In addition, the inventors have shown that using such signature compounds as a biomarker for cancer employs an assay which is simple, reproducible, non-invasive and inexpensive, and with minimal inconve-nience to the patient.

Advantageously, the methods of the invention provide a non-invasive means for diagnosing cancer. The methods are useful for enabling a clinician to make decisions with regards to the best course of treatment for a subject who is currently or who may suffer from cancer. It is preferred that the methods are useful for enabling a clinician to decide how to treat a subject who is currently suffering from the cancer. In addition, the methods are useful for monitoring the efficacy of a putative treatment for the relevant cancer. For example, treatment may comprise administration of chemo-therapy, chemoradiotherapy and/or radiotherapy with or without surgery.

In the second aspect, the subject may be being treated with a therapeutic agent and/or radiotherapy, may be on a specialised diet and and/or may have been treated with surgery. The therapeutic agent may be a chemotherapeutic agent.

In the third aspect, treating the subject may comprise administering or having administered, to the subject, a therapeutic agent and/or radiotherapy, putting the subject on a specialised diet and and/or treating the subject with surgery. The therapeutic agent may be a chemotherapeutic agent.

Hence, the methods defined herein are useful for provid-ing a prognosis of the subject's condition, such that the clinician can carry out the treatment. The methods are therefore very useful for guiding a treatment regime for the clinician, and to monitor the efficacy of such a treatment regime. The clinician may use the methods disclosed herein in conjunction with existing diagnostic tests to improve the accuracy of diagnosis.

The subject may be any animal of veterinary interest, for instance, a cat, dog, horse etc. However, it is preferred that the subject is a mammal. Preferably, the subject is a human. The subject may be either male or female.

Preferably, a sample is taken from the subject, and the level of the signature compound in the bodily sample is then measured.

The signature compounds, which are detected, are known as volatile organic compounds (VOCs), which lead to a fermentation profile, and they may be detected in the bodily sample by a variety of techniques. In one embodiment, these compounds may be detected within a liquid or semi-solid sample in which they are dissolved. In a preferred embodi-ment, however, the compounds are detected from gases or vapours. For example, as the signature compounds are VOCs, they may emanate from, or form part of, the sample, and may thus be detected in gaseous or vapour form.

The method may comprise extracting the sample from the test subject. The method may comprise using a needle or syringe or the like to extract the sample. The method may comprise depositing the sample in a sample collection container. The sample may be liquid, gaseous or semi-solid.

Preferably, the sample is any bodily sample into which the signature compound is present or secreted. For example, the sample may comprise urine, faeces, hair, sweat, saliva, blood or tears. The inventors believe that the VOCs are breakdown products of other compounds found within the blood. In one embodiment, blood samples may be assayed for the signature compound's levels immediately. Alterna-tively, the blood may be stored at low temperatures, for example in a fridge or even frozen before the level of signature compound is determined. Measurement of the signature compound in the bodily sample may be made on whole blood or processed blood.

In other embodiment, the sample may be a urine sample. It is preferred that the level of the signature compound in the bodily sample is measured in vitro from a urine sample taken from the subject. The compound may be detected from gases or vapours emanating from the urine sample. It will be appreciated that detection of the compound in the gas phase emitted from urine is preferred.

It will also be appreciated that "fresh" bodily samples may be analysed immediately after they have been taken from a subject. Alternatively, the samples may be frozen and stored. The sample may then be de-frosted and analysed at a later date.

Most preferably, however, the bodily sample may be a breath sample from the test subject. The sample may be collected by the subject performing exhalation through the mouth, preferably after nasal inhalation. Preferably, the sample comprises the subject's alveolar air. Preferably, the alveolar air was collected over dead space air by capturing end-expiratory breath. VOCs from breath bags are then preferably pre-concentrated onto thermal desorption tubes by transferring breath across the tubes.

The difference in level of signature compound may be an increase or a decrease compared to the reference. As described in the examples, the inventors monitored the level of the signature compounds in numerous patients who suffered from either oesophagogastric cancer, and compared them to the level of these same compounds in individuals who did not suffer from oesophagogastric cancer (i.e. reference or controls). They demonstrated that there was a statistically significant increase or decrease in the level of these compounds in the patients suffering from oesophagogastric cancer.

It will be appreciated that the level of signature compound in patients suffering from oesophagogastric cancer may be highly dependent on a number of factors, for example how far the cancer has progressed, and the age and gender of the subject. It will also be appreciated that the reference level of a signature compound in individuals who do not suffer from oesophagogastric cancer may fluctuate to some degree, but that on average over a given period of time, the level tends to be substantially constant. In addition, it should be appreciated that the level of a signature compound in one group of individuals who suffer from oesophagogastric cancer may be different to the level of that compound in another group of individuals who do not suffer from oesophagogastric cancer. However, it is possible to determine the average level of signature compound in individuals who do not suffer from the cancer, and this is referred to as the reference or 'normal' level of the signature compound. The normal level corresponds to the reference values discussed in the first and third aspects.

In one embodiment, the methods of the invention preferably comprise determining the ratio of chemicals within the breath (i.e. use other components within it as a reference), and then compare these markers to the disease to show if they are elevated or reduced.

The signature compound is preferably a volatile organic compound (VOC), which leads to a fermentation profile, and it may be detected in or from the bodily sample by a variety of techniques. Thus, these compounds may be detected using a gas analyser. Examples of suitable detector for detecting the signature compound preferably includes an electrochemical sensor, a semiconducting metal oxide sensor, a quartz crystal microbalance sensor, an optical dye sensor, a fluorescence sensor, a conducting polymer sensor, a composite polymer sensor, or optical spectrometry.

The inventors have demonstrated that the signature compounds can be reliably detected using gas chromatography, mass spectrometry, GCMS or TOF. Dedicated sensors could be used for the detection step.

The reference values for the first and third aspects may be obtained by assaying a is statistically significant number of control samples (i.e. samples from subjects who do not suffer from the cancer).

Accordingly, the inventors have realised that the difference in levels of the signature compound between the reference normal (i.e. control) and increased/decreased levels, can be used as a physiological marker, suggestive of the presence of the cancer in the test subject. It will be appreciated that if a subject has an increased/decrease level of one or more signature compounds which is considerably higher/lower than the 'normal' level of that compound in the reference, control value, then they would be at a higher risk of having the cancer, or a condition that was more advanced, than if the level of that compound was only marginally higher/lower than the 'normal' level.

The skilled technician will appreciate how to measure the levels of the signature compound in a statistically significant number of control individuals, and the level of compound in the test subject, and then use these respective figures to determine whether the test subject has a statistically significant increase/decrease in the compound's level, and therefore infer whether that subject is suffering from the cancer.

In the second aspect, the reference sample for the concentration of the at least one signature compound is from a sample taken from the subject previously. The reference sample may have been taken from the subject prior to commencing treatment.

Accordingly, the method may show if an improvement has occurred in the subject since the start of treatment.

Alternatively, or additionally, the reference sample may comprise a sample taken from the subject subsequent to commencing treatment. In some embodiments, the reference sample may comprise a plurality of samples taken from the subject at different time points subsequent to commencing treatment. The plurality of samples may also include a sample taken from the subject prior to commencing treatment. Accordingly, the method of the second aspect can determine if an improvement is ongoing.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying drawings, in which:

FIG. 1 shows Receiver Operating Characteristic (ROC) curves constructed using VOCs found to be significantly altered in breath from cancer patients in study 1 (blue) and study 2 (red).

EXAMPLE 1

The inventors conducted two studies (Study 1: n=631 samples and Study 2: n=219 samples, respectively) on breath analysis associated with oesophageal and gastric cancers.
Methods
Participant Recruitment Ethical approval was obtained (REC 14/LO/1136) and all participants provided written informed consent. Participants for this study were recruited from Imperial College Healthcare NHS Trust. Participants were recruited into two possible groups—either those with known oesophago-gastric cancer (OGC) or a non-cancer control group. The participants who entered into the non-cancer control group were recruited from the endoscopy suite at Imperial College Healthcare NHS Trust and were undergoing an upper gastrointestinal endoscopy on the day of providing an exhaled breath sample (and were found not to have oesophageal or gastric cancer). If patients were also undergoing a colonoscopy at the same time (and had received bowel preparation medications) they were not eligible to participate in the study. The participants who entered into the OGC group were patients who had a biopsy proven invasive gastric or oesophageal adenocarcinoma. These patients were recruited from three possible locations—either on the day of undergoing a diagnostic upper gastrointestinal endoscopy, on the day of having a staging laparoscopy and upper gastrointestinal endoscopy under general anaesthetic (part of the routine staging investigations for OGC), or on the day of review in the outpatient clinic. Patients who had already received surgical or oncological (chemotherapy or radiotherapy) treatment for the oesophageal or gastric cancer were not eligible to participate in the study. Participants were between the ages of 18 and 90, and were excluded if they were known to have liver disease (including oesophageal varices and known portal hypertension), an acute infection, another type of cancer presently or within the past 5 years, or known inflammatory conditions of the small or large bowel.

Breath Sample Collection

Exhaled breath samples were collected using a standardised breath-sampling device, 'Respiration Collector for In Vitro Analysis' (ReCIVA™) (Owlstone Medical, Cambridge, UK) in combination with a dedicated clean air supply 'Clean Air Supply Pump for ReCIVA' (CASPER) (Owlstone Medical, Cambridge, UK). All participants were fasted for a minimum of four hours and rested for 20 minutes prior to exhaled breath sample collection.

Two studies were performed. For study one, four sampling thermal desorption (TD) tubes (Tenax/Carbograph-5TD, Markes International Ltd, Llantrisant, UK) were used per participant. For study two, one sampling TD tube (Tenax/Carbograph-5TD, Markes International Ltd, Llantrisant, UK) was used per participant. Prior to sample collection all TD tubes were conditioned for 40 minutes at 330° C. using a TC-20 tube conditioner (Markes International Ltd, Llantrisant, UK). The TD tubes were stored in an airtight polypropylene container at room temperature and used for sample collection within 24 hours of conditioning.

Exhaled breath collection was performed using a standardised protocol with the participant performing normal tidal respiration whilst seated. For study one exhaled breath sample collection with the ReCIVA device was performed using a sample volume 250 ml per TD tube, and a sample flow rate of 400 ml/min. For study two exhaled breath sample collection with the ReCIVA device was performed using a sample volume 500 ml per TD tube, and a sample flow rate of 200 ml/min. Prior to analysis TD tubes were stored in an airtight polypropylene container at room temperature and all TD tubes were analysed within 12 hours of breath sample collection. TD tubes that had been conditioned in preparation for exhaled breath sample collection and subsequently not used (due to a lower than expected number of participants being recruited were) analysed concurrently with the exhaled breath samples as 'blank' TD tubes.

Analysis with TD-GC-MS

The exhaled breath and blank TD tubes samples were analysed using TD-GC-MS. The TD tubes were desorbed using a Markes TD-100 thermal desorption unit (Markes International Ltd, Llantrisant, UK) using a two stage desorption programme, applying a constant flow of helium at 50 ml/min. In the primary desorption stage, TD tubes were dry-purged for 3 min and heated at 280° C. for 10 min. In the secondary desorption stage, the cold trap (U-T12ME-2S, Markes International Ltd, Llantrisant, UK) was rapidly (99° C./min) heated to from 10° C. to 290° C. VOCs were transferred from the TD unit to the GC by means of a capillary line heated at 140° C. GC-MS analysis was performed using an Agilent 7890 B GC with 5977A MSD (Agilent Technologies Ltd, Santa Clara, USA) equipped with a ZB-642 capillary column (60 m×0.25 mm ID×1.40 um df; Phenomenex Inc, Torrance, USA) with helium used as the carrier gas (1.0 ml/min flow rate). The GC column temperature programme was set as follows: 4 min at 40° C., ramp to 100° C. at 5° C./min with a 1 min hold, ramp to 110° C. at 5° C./min with a 1 min hold, ramp to 200° C. at 5° C./min with a 1 min hold and finally ramp to 240° C. at 10°

C./min with a 4 min hold. The MS transfer line temperature was 240° C. and EI source conditions were 70 eV at 230° C. Mass acquisition was carried out in the range 20-250 m/z with a rate of approximately 6 scans/s-1.

Results

In breath, biological signatures are usually obscured by intra- and inter-subject variability, experimental conditions, e.g. ambient air quality, etc. Most of the time biologically relevant compounds are present in very low abundances. To mitigate this, large number of samples were collected, as outlined above. It was possible to predict OGC with high accuracy in both studies and identify the corresponding metabolomic "fingerprint". The results are shown in tables 1 and 2 below.

TABLE 1

Biomarkers identified that were found to be significantly altered in breath from cancer patients and corresponding p values in study 1

| p-values | VOC | Logarithm fold changes |
|---|---|---|
| 0.00019 | methyl 2,3,5,6-tetra-O-methyl-α-D-galactofuranoside | -0.56777 |
| 0.00019 | 4-hydroximino-2,2,6,6-tetramethyl-1-piperidinyl ester 4-amino-benzoic acid | 0.60436 |
| 0.00018 | 1-tetradecanol | -1.2674 |
| 0.00016 | N-butyl-benzenesulfonamide | -0.71766 |
| 0.00015 | hexadecanoic acid | -0.87638 |
| 8.95E-05 | tetradec-5-yl ester 3,5,5-trimethyl-hexanoic acid | -0.91395 |
| 4.81E-05 | 4,4-dimethyl-octane | 0.31272 |
| 4.45E-05 | tetradecyl ester undec-10-ynoic acid | -0.5371 |
| 4.14E-05 | 1-dotriacontanol | -1.3416 |
| 2.86E-05 | Benzyl 3-deuterio-α-diazopropionate | 0.8055 |
| 9.40E-06 | 1-methylethyl ester formic acid | 1.0375 |
| 5.31E-06 | 1-chloro-tetradecane | -0.85828 |
| 5.10E-06 | 4-methyloctan-1-ol | -0.4607 |
| 4.27E-06 | carbon monoxide; nickel | -0.5693 |
| 5.66E-07 | 2-ethyl-cyclohexylamine | -0.81605 |

TABLE 2

Biomarkers identified that were found to be significantly altered in breath from cancer patients and corresponding p values in study 2

| p-values | VOC | Logarithm fold changes |
|---|---|---|
| 3.41E-08 | 3-ethyl-1-octene | -1.3811 |
| 3.31E-08 | ethyl lactate | -1.6347 |
| 2.32E-08 | tetramethyl succinimide | -0.75236 |
| 9.05E-09 | 6-methyl-2-heptanone | -2.8561 |
| 8.62E-09 | (E)-ethen-2-d-ol | -2.5854 |
| 5.58E-09 | 4-anilino-4-keto-2-phenyl-butyric acid | -1.889 |
| 1.94E-09 | Diisobutyl (oxybis(ethane-2,1-diyl))dicarbonate | -1.9607 |
| 1.50E-09 | nickel tetracarbonyl | -1.5801 |
| 9.98E-10 | (E)-2-ethylene-4-methylene-5-hexenal | -1.5124 |
| 7.39E-10 | 3-methyl-1-butyne | -1.7809 |
| 2.84E-10 | (R)-5-methyl-2-(1-methylethylidene)-cyclohexanone | -1.8082 |
| 1.27E-10 | α-propyl-benzeneethanol | -3.4456 |
| 1.06E-10 | 4-methyl-1-pentene | -3.1494 |
| 4.87E-11 | 1,3,3-trimethyl-2-oxabicyclo[2.2.2]oct-5-ene | -1.68 |
| 2.52E-11 | 2,2'-(ethene-1,2-diylbis(sulfanediyl))diethanol | -2.0075 |
| 2.24E-11 | 3-methyl-thiophene | -2.4387 |
| 3.50E-12 | butanal | -3.1176 |
| 1.57E-12 | Tert-butyl alcohol | -4.5814 |
| 5.93E-14 | 2-Methoxysuccinonitrile | -5.4045 |

A negative value for the log fold change indicates that the VOC increases in a sample from a patient with cancer.

Conversely, a positive value for the log fold change indicates that the VOC decreases in a sample from a patient with cancer.

ROC plots (see FIG. 1) were constructed using the VOCs for studies 1 and 2, respectively. The ROC plot for study 1 biomarkers produced an AUC of 0.902 for distinguishing Cancer vs. Non-Cancer and for study 2 biomarkers the AUC was 0.740.

The invention claimed is:

1. A method of treating an individual suffering from oesophagogastric cancer, said method comprising the steps of:

a) detecting the level of at least one signature compound in a bodily sample from a test subject using gas chromatography, mass spectrometry, and/or GCMS, wherein the bodily sample is a breath sample from the test subject, wherein the at least one signature compound is elected from group (i) consisting of methyl 2,3,5,6-tetra-O-methyl-α-D-galactofuranoside; 1-tetradecanol; N-butyl-benzenesulfonamide; hexadecanoic acid; tetradec-5-yl ester 3,5,5-trimethyl-hexanoic acid; tetradecyl ester undec-10-ynoic acid; 1-dotriacontanol; 1-chloro-tetradecane; 4-methyloctan-1-ol; carbon monoxide; nickel; 2-ethyl-cyclohexylamine; 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediyl))diethanol; 3-methyl-thiophene; tert-butyl alcohol; and 2-methoxysuccinonitrile, compared to the reference, in the bodily sample from the test subject, or group (ii) consisting of 4-hydroximino-2,2,6,6-tetramethyl-1-piperidinyl ester 4-amino-benzoic acid; 4,4-dimethyl-octane; benzyl 3-deuterio-α-diazopropionate; and 1-methylethyl ester formic acid; and b) treating the test subject with a therapeutic agent and/or radiotherapy, if there is an increase in the level of the at least one signature compound selected from group (i) or a decrease in the level of the at least one signature compound selected from group (ii) in the bodily sample from the test subject, compared to a reference, wherein the reference level is the level of the at least one signature compound in an individual, or the average level for a group of individuals, wherein the individual or group of individuals do not suffer from oesophagogastric cancer, wherein the treatment reduces or delays progression of cancer and/or treats cancer.

2. A method according to claim 1, wherein the at least one signature compound is selected from the group consisting of methyl 2,3,5,6-tetra-O-methyl-α-D-galactofuranoside; 4-hydroximino-2,2,6,6-tetramethyl-1-piperidinyl ester 4-amino-benzoic acid; 1-tetradecanol; N-butyl-benzenesulfonamide; hexadecanoic acid; tetradec-5-yl ester 3,5,5-trimethyl-hexanoic acid; 4,4-dimethyl-octane; tetradecyl ester undec-10-ynoic acid; 1-dotriacontanol; benzyl 3-deuterio-α-diazopropionate; 1-methylethyl ester formic acid; 1-chloro-tetradecane; 4-methyloctan-1-ol; carbon monoxide; nickel; and 2-ethyl-cyclohexylamine.

3. A method according to claim 2, wherein the at least one signature compound is selected from the group consisting of methyl 2,3,5,6-tetra-O-methyl-α-D-galactofuranoside; 4-hydroximino-2,2,6,6-tetramethyl-1-piperidinyl ester 4-amino-benzoic acid; 1-tetradecanol; N-butyl-benzenesulfonamide; hexadecanoic acid; tetradec-5-yl ester 3,5,5-trimethyl-hexanoic acid; 4,4-dimethyl-octane; tetradecyl ester undec-10-ynoic acid; 1-dotriacontanol; and benzyl 3-deuterio-α-diazopropionate.

4. A method according to claim 3, wherein the at least one signature compound is selected from the group consisting of methyl 2,3,5,6-tetra-O-methyl-α-D-galactofuranoside; 4-hydroximino-2,2,6,6-tetramethyl-1-piperidinyl ester 4-amino-benzoic acid; 1-tetradecanol; N-butyl-benzenesulfonamide; and hexadecanoic acid.

5. A method according to claim 1, wherein the at least one signature compound is selected from the group consisting of 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; 1,3,3-trimethyl-2-oxabicyclo[2.2.2]oct-5-ene; 2,2'-(ethene-1,2-diylbis(sulfanediyl)) diethanol; 3-methyl-thiophene; tert-butyl alcohol; and 2-methoxysuccinonitrile.

6. A method according to claim 5, wherein the at least one signature compound is selected from the group consisting of 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; nickel tetracarbonyl; (E)-2-ethylene-4-methylene-5-hexenal; 3-methyl-1-butyne; (R)-5-methyl-2-(1-methylethylidene)-cyclohexanone; α-propyl-benzeneethanol; 4-methyl-1-pentene; and 1,3,3-trimethyl-2-oxabicyclo[2.2.2]oct-5-ene.

7. A method according to claim 6, wherein the at least one signature compound is selected from the group consisting of 3-ethyl-1-octene; ethyl lactate; tetramethyl succinimide; 6-methyl-2-heptanone; (E)-ethen-2-d-ol; 4-anilino-4-keto-2-phenyl-butyric acid; diisobutyl (oxybis(ethane-2,1-diyl)) dicarbonate; and nickel tetracarbonyl.

8. A method according to claim 7, wherein the at least one signature compound is selected from the group consisting of 3-ethyl-1-octene; and ethyl lactate.

9. A method according to claim 1, wherein the mass spectrometry comprises TOF.

10. A method according to claim 1, wherein the at least one signature compound is selected from the group consisting of 1-tetradecanol; 4-methyloctan-1-ol; 3-ethyl-1-octene; ethyl lactate; 6-methyl-2-heptanone; (E)-ethen-2-d-ol; (E)-2-ethylene-4-methylene-5-hexenal; 3-methyl-1-butyne; 4-methyl-1-pentene; 3-methyl-thiophene; tert-butyl alcohol; and 4,4-dimethyl-octane.

\* \* \* \* \*